(12) United States Patent
Giometti

(10) Patent No.: US 6,510,751 B2
(45) Date of Patent: Jan. 28, 2003

(54) GLASS CONTAINER INSPECTION MACHINE

(75) Inventor: Stephen M. Giometti, Horseheads, NY (US)

(73) Assignee: Emhart Glass S.A., Cham (CH)

( * ) Notice: Subject to any disclaimer, the term of this patent is extended or adjusted under 35 U.S.C. 154(b) by 37 days.

(21) Appl. No.: 09/747,501

(22) Filed: Dec. 21, 2000

(65) Prior Publication Data

US 2002/0078769 A1 Jun. 27, 2002

(51) Int. Cl.[7] .................................................. B07C 5/34
(52) U.S. Cl. ...................................................... 73/865.8
(58) Field of Search .................. 73/865.8; 209/524–533

(56) References Cited

U.S. PATENT DOCUMENTS 3,250,388 A * 5/1966 Eggers ....................... 209/532
3,383,483 A * 5/1968 Johnson ..................... 209/533
4,278,173 A * 7/1981 Pemberton et al. ......... 209/532

* cited by examiner

Primary Examiner—Robert Raevis
(74) Attorney, Agent, or Firm—Spencer T. Smith

(57) ABSTRACT

A glass container inspection machine has a machine frame to which an inspection device is secured. The inspection device includes a vertical track member, a car vertically displaceable along the vertical track member, a servo operated drive pulley system secured to the vertical track member for vertically displacing the car, an inspection head interconnected with the car for linear, relative displacement and clampable at a desired position. The inspection device is mounted on the frame so that the linear displacement of the inspection head will enable the head to be adjusted to be concentric with the finish of bottles having radially different axes.

2 Claims, 3 Drawing Sheets

GLASS CONTAINER INSPECTION MACHINE

The present invention relates to glass container inspection machines and more particularly to such machines which use star wheel conveyors.

BACKGROUND OF THE INVENTION

A conventional way of inspecting bottles which are being carried along a linear conveyor is to utilize a star wheel conveyor to transfer the bottles from the linear conveyor to a table beneath the star wheel conveyor, displace the bottles, in a circular path, across the table through a number of inspection stations which could include a station for inspecting the outer and inner diameters of the finish (ring and plug respectively) or inspecting for DIP and height and then replace them on the conveyor.

In such an inspection device, an inspection head must be lowered precise distances in order for the inspections to occur properly. To set up the inspection device, a bottle is located at the inspection position and the inspection head is lowered to teach the control the correct down inspection positions).

OBJECT OF THE INVENTION

It is accordingly an object of the present invention to provide a glass container inspection machine having a star wheel feeder wherein plug and ring inspections will take place which will be very quick to set up.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE PREFERRED EMBODIMENT

Figure 1:
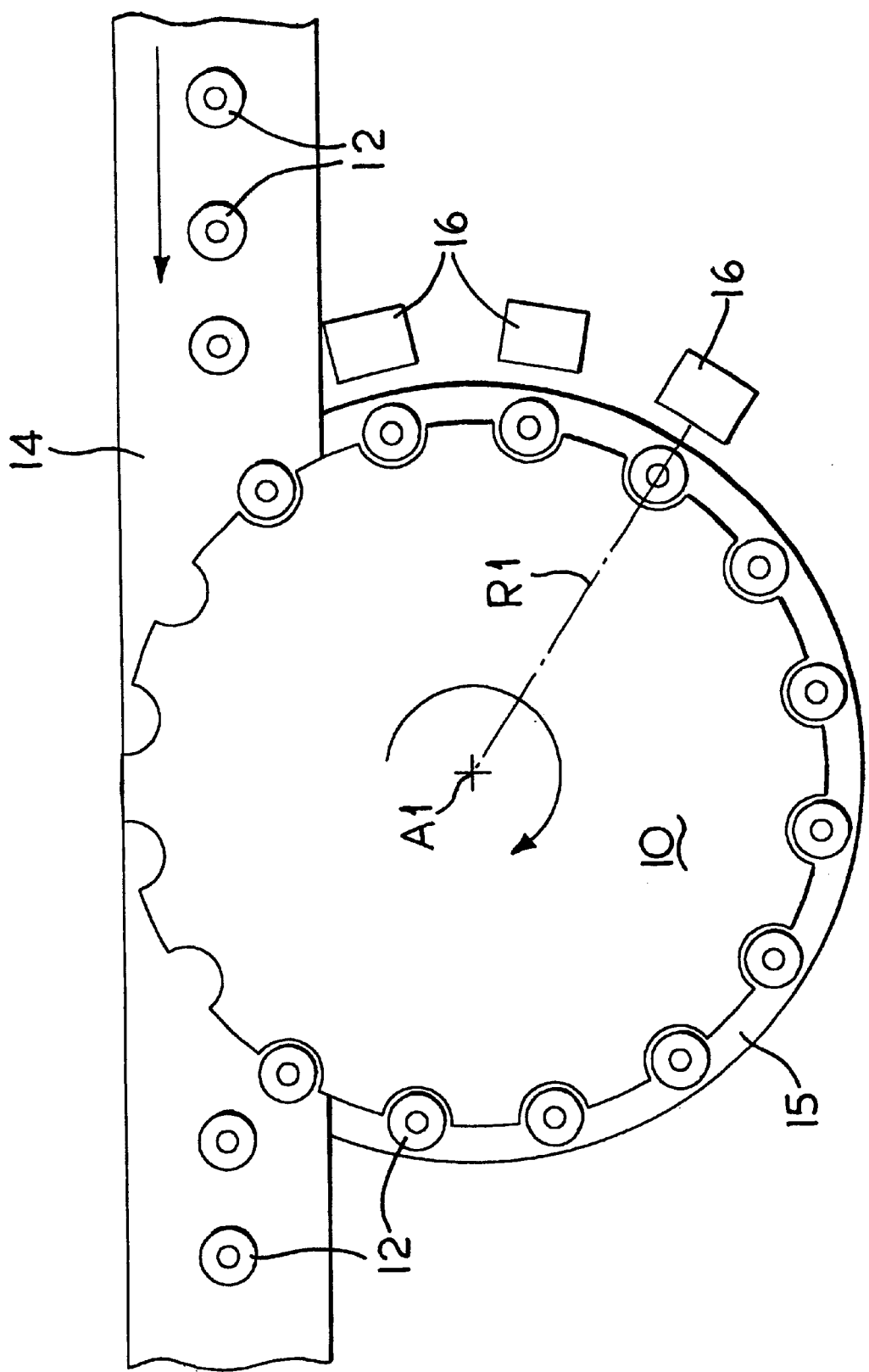
FIG. 1 is a top schematic view of a glass container inspection machine which has a star wheel feeder.
Figure 2:
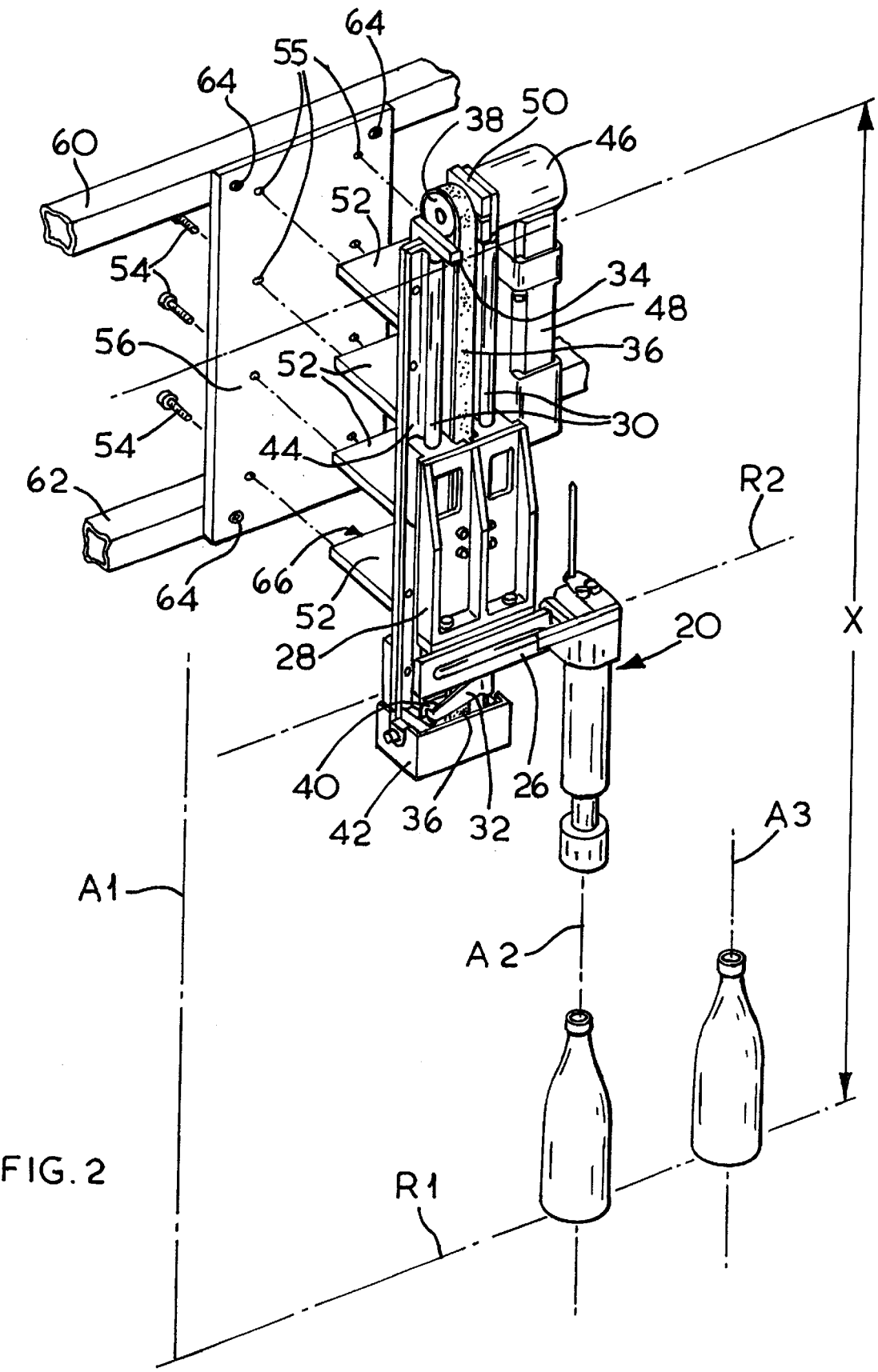
FIG. 2 is an oblique elevational view illustrating an inspection device shown separated from a mounting plate to which it is secured.

A glass container inspection machine includes a star wheel feeder assembly 10 which is rotatively driven about axis A1 in clockwise angular steps to transfer bottles 12 from a linear conveyor 14 (as shown the conveyor is carrying bottles right to left) onto an annular table 15 where they will be incrementally displaced to a series of inspection stations 16. Ultimately the bottle is released to the conveyor. The inspection device 20 shown in figure two (a plug/ring, DIP or height inspection device, for example) is located to inspect a bottle when it is stopped by the star wheel feeder at R1.

The inspection device 20 is mounted on a horizontal slider 26 interconnected to a car 28, which is displaceable along a pair of vertical rails 30. This interconnection permits displacement of the slider, relative to the car along radius R2, when clamp 32 is released. The car is displaceable vertically between a fixed fully up position defined by an adjustable hard stop 34 and a programmed down position(s) by a belt 36 which is connected to the car and which extends between a driven pulley 38 at the top and an idler pulley 40 at the bottom which is mounted on a support bracket 42 secured to the end of a vertical plate 44 which includes the rails 30.

The encoder mounted on the servo motor can be used by the servo control to determine the exact displacement down from the fixed hard stop and because the hard stop is always a fixed distance away from the table surface 15 the location of the mechanism relative to the table surface is known. When a given bottle is to be run in the inspection machine, the control can accordingly be programmed by inputting the bottle height to position the mechanism just above the finish to clear the bottle for loading/unloading into the inspection position. Then the control can be programmed, depending on bottle shape, to lower the mechanism to one or more inspection heights. Upon completion of the inspection(s) the mech will be displaced upwardly to the original ready position above the finish and the next bottle can be advanced to the inspection station. Accordingly, by simply entering a bottle height and stroke setting, and by moving the mechanism along R2 until the inspection device is aligned with the finish, the mechanism will be fully set up. This enables the set up to be done very fast and very efficiently.

The driven pulley is driven by a right angle gearbox 46 which is powered by a servomotor 48. A motor bracket 50 mounts the motor/gearbox/driven pulley on the vertical plate 44. The vertical plate 44 is secured to a number of horizontal brackets 52 and these horizontal brackets are secured to a vertical frame plate 56 by suitable screws 54 which pass through holes 55 in the frame plate. The frame plate 56 is secured to square tubular beams 60,62, which are part of the frame of the inspection machine, by screws 64. The entire plug and dip assembly is accordingly mounted above the bottles as they are processed through the inspection device.

The rear edge 66 of a horizontal bracket 52 is square with the frame (frame plate and tubular beams) whereas the front edge of a horizontal plate is parallel to radius R2 which is parallel to and vertically above radius R1 (R1 is the radius that extends from the central axis A1 of the feed wheel and intersects the axis of a bottle located by the star wheel at one of the inspection stations—as shown in FIG. 1, R1 is located approximately at 4:00. The star wheel can, depending on the size of the bottle and the size of the star wheel, locate the axis of the bottle at different positions (A2,A3) along R1). The angle between the frame and the front edge of these horizontal brackets will depend on the station at which this inspection device is situated. The angle of the front edge is selected to locate the linear motion of the head parallel to and vertically above R1. When the size of the bottle or the size of the star wheel changes the head portion 22 can accordingly be radially displaced to locate its axis centrally within the finish of the bottle to be inspected.

Figure 3:
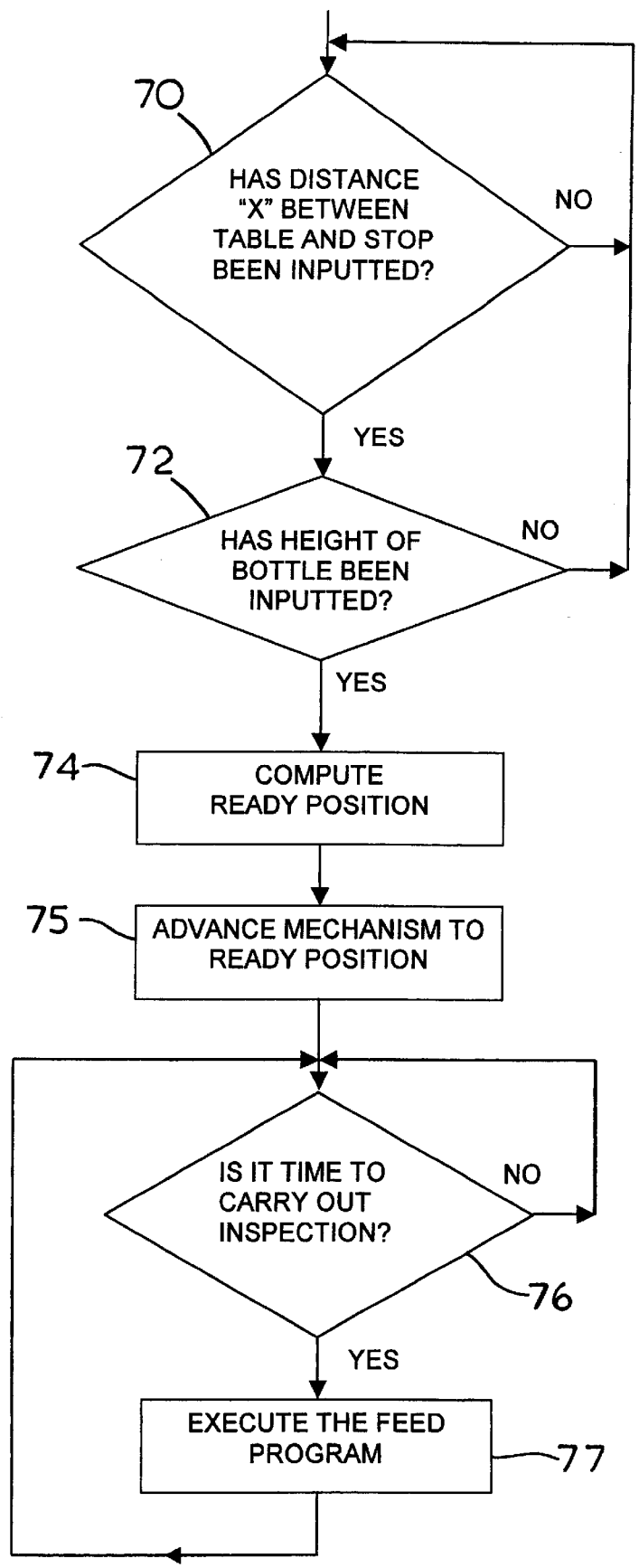
FIG. 3 is a logic diagram illustrating the operation of the control for the inspection device.

FIG. 3 illustrates the control for the plug and dip inspection device. Since the upper stop height and the height of the top surface of the table 15 can be determined, the control will know the answer to the query: "Has Distance X Between Table And Stop Been Defined?" 70. This could be resolved by inputting the distance or by inputting each dimension with the control differencing the numbers. The control can then answer the query: "Has Height Of Bottle Been Inputted? 72". This too can be done in a variety of ways. The actual height could be inputted or the name of the bottle could be inputted with the computer looking up the height in a table of some kind. If the answer is affirmative, the control can Compute Ready Position 74 and Advance Mechanism To Ready Position 75. When the query "Is It Time To Carry Out Inspection" 76 is answered in the affirmative, the control will Execute The Feed Program 77 which could lower the mechanism to one or more positions before the inspection is completed and the mechanism is again raised to the ready position.

What is claimed is:

1. A glass container inspection machine for inspecting a bottle having a selected height comprising
   a machine frame,
   an inspection device including
      a vertical track member supported by said frame and having an upper fixed stop,
      a car vertically displaceable along said vertical track member,
      drivable means secured to said vertical track member for vertically displacing said car,
      motor means secured to said drivable means for driving said drivable means,
      an inspection head interconnected with said car, and
   a table having a top surface for supporting a glass container as the glass container is delivered to the inspection device,
   a control for operating said motor means to downwardly displace said inspection head to a ready position, said control comprising means for defining said ready position from data including first data indicative of the distance between said fixed stop and the top surface of said table and second data indicative of the height of the bottle.

2. A glass container inspection machine comprising
   a machine frame,
   an inspection device for inspecting a bottle displaced in a circular path to an inspection location including
      a vertical track member,
      a car vertically displaceable along said vertical track member,
      drivable means secured to said vertical track member for vertically displacing said car,
      motor means secured to said drivable means for driving said drivable means,
      an inspection head interconnected with said car for linear, relative displacement, and
      means for clamping said inspection head to said car at a desired relative position, and
   mounting means for mounting said inspection device on said machine frame so that the linear displacement of said inspection head will enable the head to be adjusted to be concentric with the axis of the finish of bottles having parallel axes located on the radius of the circular path defining the inspection location.

\* \* \* \* \*